(12) United States Patent
Bäck

(10) Patent No.: US 7,713,254 B2
(45) Date of Patent: May 11, 2010

(54) SANITARY ABSORBENT ARTICLE INCLUDING A FASTENER

(75) Inventor: Lucas Bäck, Göteborg (SE)

(73) Assignee: SCA Hygiene Products AB, Gothenburg (DE)

( * ) Notice: Subject to any disclaimer, the term of this patent is extended or adjusted under 35 U.S.C. 154(b) by 442 days.

(21) Appl. No.: 10/177,601

(22) Filed: Jun. 24, 2002

(65) Prior Publication Data
US 2003/0014033 A1   Jan. 16, 2003

Related U.S. Application Data

(60) Provisional application No. 60/301,774, filed on Jun. 28, 2001.

(51) Int. Cl.
*A61F 13/15* (2006.01)
*A61F 13/20* (2006.01)

(52) U.S. Cl. ............ 604/391; 604/386; 604/392

(58) Field of Classification Search ......... 604/386–392
See application file for complete search history.

(56) References Cited

U.S. PATENT DOCUMENTS 5,053,028 A    10/1991   Zoia et al.
5,624,429 A *  4/1997   Long et al. ............ 604/391
5,669,901 A *  9/1997   LaFortune et al. ...... 604/391
5,722,968 A    3/1998   Datta et al.

FOREIGN PATENT DOCUMENTS

EP        0 959 857 B1    11/2002
SE          504 624        3/1997
WO        WO 99/13745     3/1999

* cited by examiner

*Primary Examiner*—Michele Kidwell
(74) *Attorney, Agent, or Firm*—Buchanan Ingersoll & Rooney PC

(57) ABSTRACT

A sanitary, absorbent article includes a hooks and loops type fastener for releasably attaching a first and a second part of the article to each other, wherein the first part is overlapping the second part when the parts are attached to each other, with a hooks member affixed to said first part of the article and a loops member affixed to the second part of the article. Each member has a base portion having a bottom surface affixed to the first or second part of the article and an opposite top surface containing hooks elements and loops elements, respectively. The fastener can include a first end region distal to the overlapping edge of the first part, in which the engagement force between the hooks and loops element of the members is reduced.

18 Claims, 3 Drawing Sheets

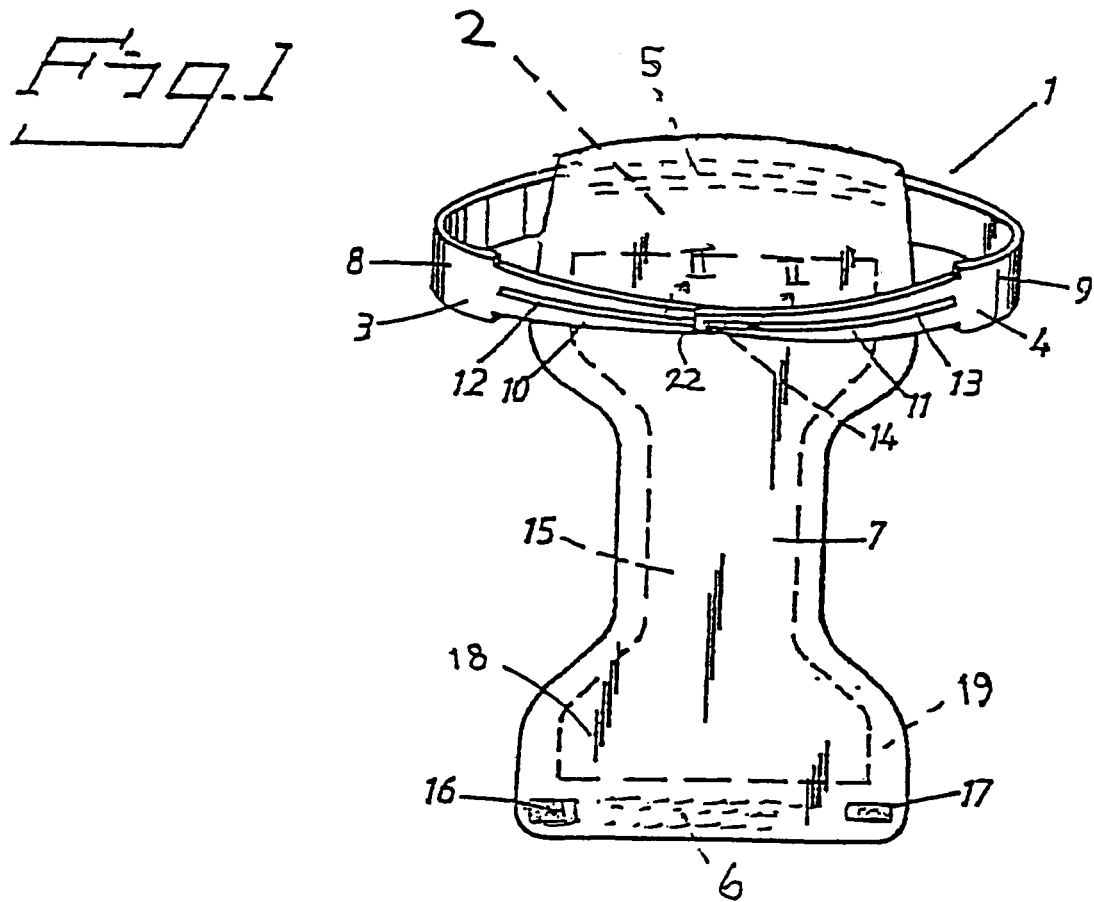
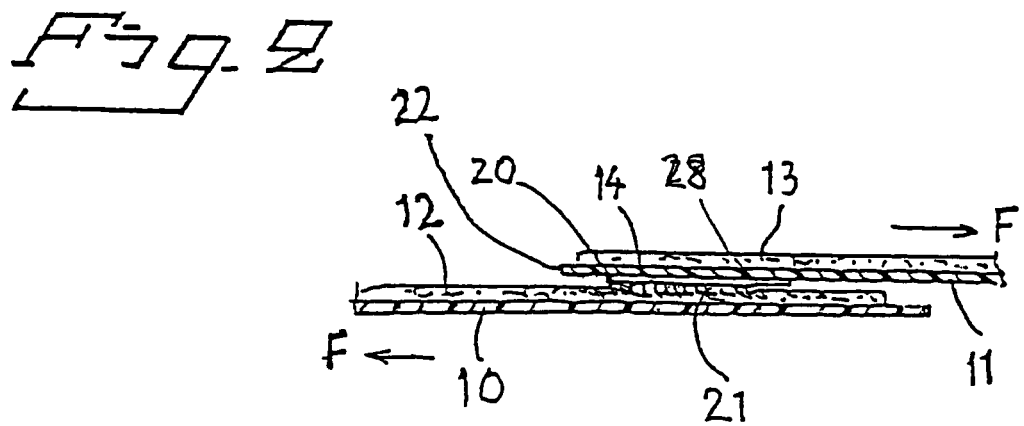

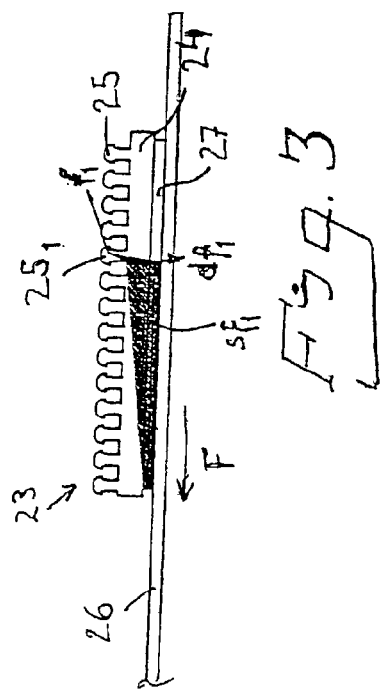
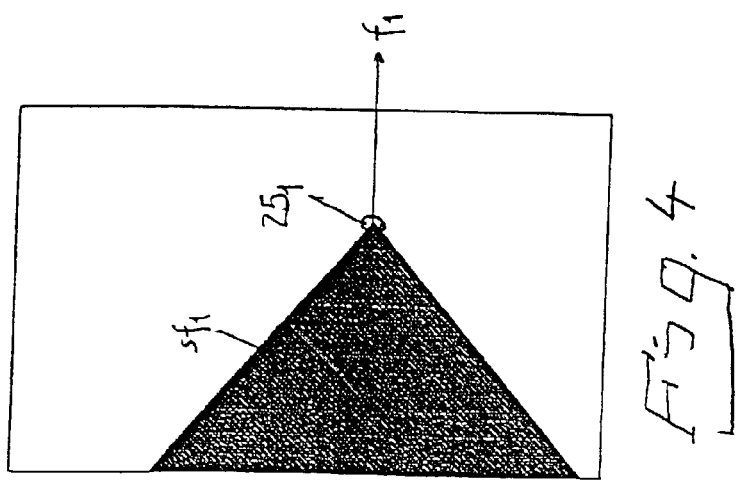
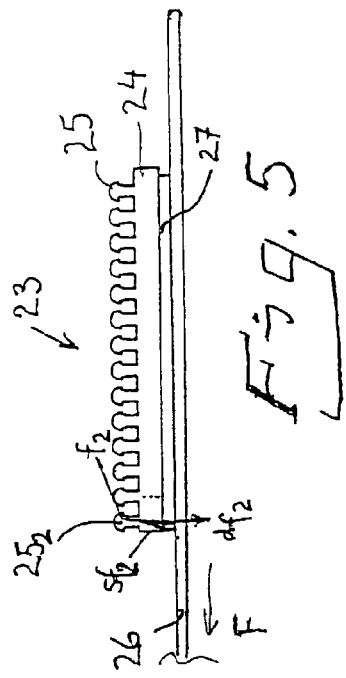
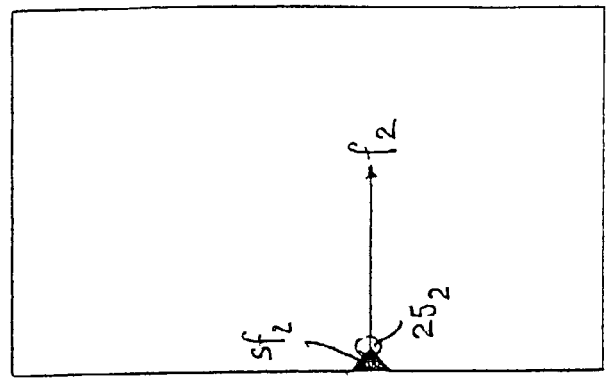

SANITARY ABSORBENT ARTICLE INCLUDING A FASTENER

CROSS-REFERENCE TO RELATED APPLICATIONS

The present application claims the priority under 35 U.S.C. §120 of U.S. Provisional Application No. 60/301,774, filed in the United States on Jun. 28, 2001, the entire contents of which are hereby incorporated herein by reference.

BACKGROUND OF THE INVENTION

Field of the Invention

The present invention relates to a sanitary, absorbent article including at least one hooks and loops type fastener for releasably attaching a first and a second part of the article to each other, wherein the first part is overlapping the second part when said parts are attached to each other, the fastener including a hooks member affixed to said first part of the article and a loops member affixed to said second part of the article, each member comprising a base portion having a bottom surface affixed to the first or second part of the article and an opposite top surface containing hooks elements and loops elements, respectively.

Fastener of the hooks and loops type are nowadays often used to releasably attach different parts of sanitary absorbent articles to each other, such as the front and rear side parts of a diaper or the end parts of a waist belt. When affixing the members of such fasteners to an irregular surface, such as the surface of a nonwoven material, delamination of the members have occurred in several cases when the articles containing the members have been subjected to loads corresponding to the loads during normal use of the article.

An object of the present invention is to eliminate or at least to a great extent reduce the risk for delamination of fasteners of the hooks and loops type.

SUMMARY OF THE INVENTION

This object is achieved by a sanitary, absorbent article including a hooks and loops type fastener for releasably attaching a first and a second part of the article to each other, wherein the first part is overlapping the second part when said parts are attached to each other, the fastener includes a hooks member affixed to said first part of the article and a loops member affixed to said second part of the article, each member comprising a base portion having a bottom surface affixed to the first or second part of the article and an opposite top surface containing hooks elements and loops elements, respectively, characterised in that the fastener has a first end region in which the engagement force between the hooks and loops element of the members is reduced. Thereby a reduction of the delamination force, i.e. the force component directed perpendicular to the plane of the second part of the article, is accomplished.

In a preferred embodiment the first end region of the fastener has a width of 3-8 mm, preferably 5 mm and the hooks member is without hooks elements in the first end region.

Alternatively the loops member is without loops elements in a portion thereof complementary to the first end region of the hooks member.

In a second embodiment the hook elements of the hooks member are made non-engageable with the loops elements of the loops member or vice versa in the portion of the fastener in which the first end region of the hooks member is disposed.

The hooks member may in both embodiments be affixed to a nonwoven material.

BRIEF DESCRIPTION OF THE DRAWINGS

The present invention will now be described with reference to the following figures.

FIG. 1 discloses schematically an incontinence garment according to a first embodiment of the invention in a perspective view.

FIG. 2 disclose a sectional view along line II-II of FIG. 1.

FIGS. 3 and 4 disclose schematically the forces acting on a conventional hooks member of a fastener of the hooks and loops type in the middle in a side view and in a plan view, respectively.

FIGS. 5 and 6 disclose schematically the forces acting on a conventional hooks member of a fastener of the hooks and loops type in the edge portion in a side view and in a plan view, respectively.

DETAILED DESCRIPTION OF THE PREFERRED EMBODIMENTS

Figure 7:
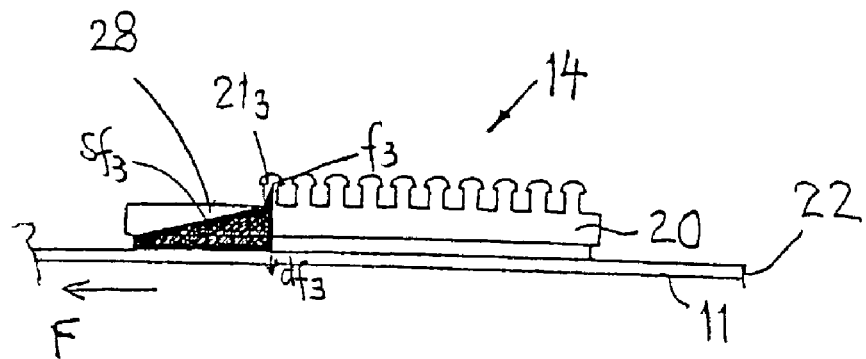
FIGS. 7 and 8 disclose schematically the forces acting on a hooks member according to an embodiment of the invention in a side view and a plan view, respectively.

FIG. 1 shows an incontinence garment comprising a waist belt 1 and an incontinence guard 7. The waist belt 1 illustrated in FIG. 1 is made of a flexible material, preferably a nonwoven, and includes a rear portion 2 of the incontinence guard 7 and two front portions 3,4 affixed to the respective left and right side parts of the rear portion 2. The rear portion 2 comprises further an elastic waist element 5, for example elastic threads, which is attached to the rear portion 2 in a stretched state as is conventional for this type of article. The waist part of the front portion of the guard 7 is also made elastic in the same way by an elastic waist element 6.

The waist-belt front portions 3,4 include a relatively broad rear part 8 and 9 respectively, which connect with the rear portion and stretch over the hips of the wearer in use. Narrow, elongated and rectangular fastener members 12 and 13 extend along the longitudinal symmetry lines of the tapering portions 10, 11, these fastener members preferably comprising loop-bearing material. A fastener member 14 complementary to the fastener member 12, preferably a piece of hook-bearing material, is attached to the inside of the tapering portion 11 at the end part thereof. FIG. 1 shows the belt when fastened together, i.e. with the fastener member 14 in engagement with the fastener member 12. As will be understood, because the member 12 extends along substantially the full length of the tapering portion 10, the illustrated waist belt can be adjusted to fit around the waist of many users having mutually different waist sizes.

The incontinence guard 7 has in the front part thereof two fastener members 16,17 complementary to the fastener members 12,13 on the waist belt 1, the members 16, 17 preferably being pieces of hooks-bearing material. The incontinence guard comprises in a conventional manner an absorbent core 15 being enclosed between a liquid-permeable surface layer 18 and a liquid-impermeable surface layer 19, the members 16,17 being affixed to the liquid-permeable surface material 18. All materials known to be used for the components of a diaper or an incontinence guard can be used for the incontinence guard 7, such as a layer 18 of nonwoven, a body 15 of cellulose fluff pulp containing superabsorbent particles or not and a laminate 19 of a nonwoven and a vapour permeable film.

In FIG. 2 a partial sectional view of the belt 1 is schematically shown, the tapering portion 11 of the belt 1 overlapping the tapering portion 10. The piece 14 of hooks-bearing material being affixed to the inside of the tapering portion 11 is fastened to the elongate piece 12 of loops-bearing material. The forces acting on the tapering portions 10 and 11 are indicated by arrows F in FIG. 2.

The piece 14 of hooks-bearing material consists of a base portion 20 having a bottom surface affixed to the inside of tapering portion 11 of the belt 1 by gluing or heat welding and a top surface opposite from the bottom surface containing rows of hooks 21 protruding therefrom. In the disclosed embodiment, the end region of the base portion 20 being distal to the edge 22 of tapering portion 11 is without protruding hooks in order to reduce the risk for delamination of the piece 14 from the tapering portion 11 as will be explained below with reference to FIGS. 3-5. The pieces of hooks-bearing material affixed to the layer 18 in the front parts of the incontinence guard 7 are constructed in the same manner, the end regions thereof being distal to the respective left and right side edge of the incontinence guard 7 being without hooks, as schematically illustrated for the pieces 16, 17 in FIG. 1.

The risk for delamination of a piece of hooks- or loops-bearing material is due to a moment force acting on the base portion of said piece in an end region thereof. Every hook or loop of such pieces is distanced from the base portion thereof and the engagement point between a loop and a hook will therefore be distanced from the bottom of the base portion. In FIG. 3 a piece 23 of hooks-bearing material having a base portion 24 and rows of hooks 25 protruding upwardly from the base portion, is schematically shown. The engagement force acting on a hook $25_1$ when engaged with a loop (not shown for the sake of clarity) is represented by the arrow $f_1$. The large part of the force $f_1$ will be taken up in the base portion as shear forces, as indicated by the shade triangles $sf_1$ in FIGS. 3 and 4. Only a very little part of the force $f_1$ will act as a delamination force $df_1$ perpendicular to the plane of the base portion 24. However, as schematically shown in FIGS. 5 and 6, in a first end region of the piece 23 the force $f_2$ acting on a hook $25_2$ can only to a small extent be taken up as shear forces $Sf_2$ in the base portion 24 and the delamination force $df_2$ will be large compared to the force $df_1$ resulting from the force $f_1$ acting on the hook $25_1$. The piece 23 is affixed to the layer 26 being for example a nonwoven material by an adhesive layer 27. The adhesive connection between the piece 23 and the layer 26 can withstand large shear forces but the delamination forces, i.e. forces perpendicular to the plane of base portion 24, required to delaminate the first end region of the piece 23 from the layer 26 are relatively small. It is therefore a risk that the delamination forces $df_2$ will be large enough to start a delamination of the piece 23 in the first end region thereof.

Figure 8:
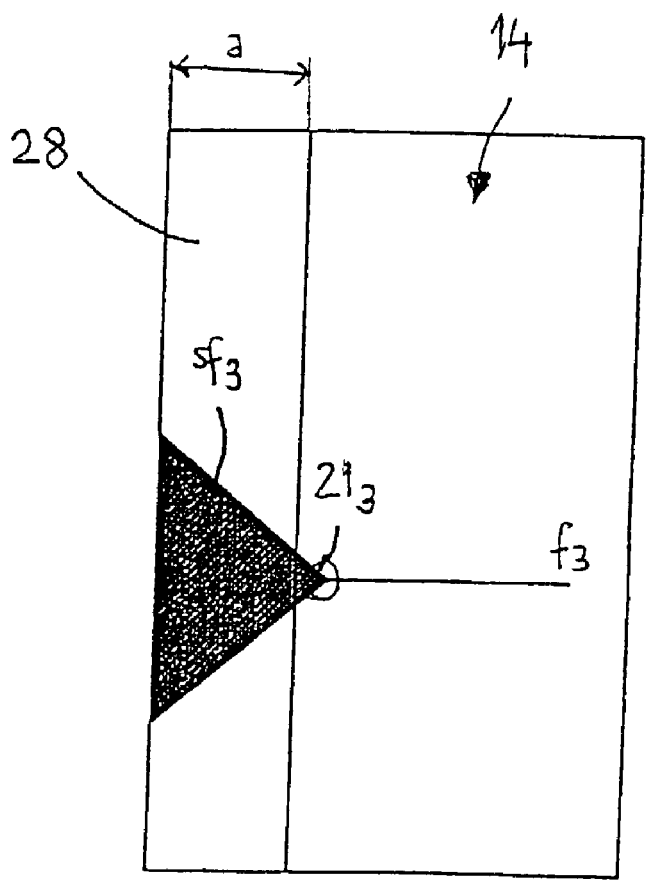

In FIGS. 7 and 8 the hooks member 14 affixed to the tapering portion 11 is schematically shown. In order to reduce the risk for delamination, this hooks member has no hooks in a first end region 28 thereof. In these Figures, the reaction forces from the force $f_3$ acting on a hook $21_3$ in the last row of hooks is schematically illustrated and it is evident that the force $f_3$ to the largest extent will be taken up as shear forces $sf_3$, only a small part being taken up as a delamination force $df_3$. The width a of the first end region 28 without hooks is 3-8 mm, preferably around 5 mm.

The forces acting on a loops member will be analogous to the forces described above for the hooks member and the loops member can be constructed in the same way as the hooks member, i.e. without loops in a first end region thereof. It is pointed out that the first end region of a loops member lies opposite to the first end region of hooks member cooperating therewith. The first end of a hooks or loops member is the end lying distal from the overlapping edge of the element to which the respective member is attached, as seen in the direction of the forces. Thus, if the fastener is subjected to forces having different directions, the respective member can have more than one first end region. However, usually it is only the greatest force that need to be considered when the risk for delamination should be eliminated or reduced.

In a described embodiment the moment force created on a first end region of a hooks and loops fastener has been reduced by providing a first end region of the hooks member without hooks. It is of course also possible to instead destroy the existing hooks in an end region of a hooks member in order to ensure that in the end region in question the hooks will not be able to engage the loops of a complementary loops member, for example by the application of heat and pressure if the hooks member is made of a heat deformable material or by cutting off the heads of the hooks.

The hooks members 16,17 on the front part of the incontinence guard 7 are preferable also provided with first end regions without hooks as schematically illustrated in FIG. 1 for the members 16,17, the first end regions thereof lying distal from the respective left and right side edge of the incontinence guard 7. The gravity forces acting on the hooks members when the article is worn are smaller than the elastic forces and need not be considered.

Fasteners of the hooks and loops type having hooks or loops members with end regions in which the hooks or loops are not engageable to each other can of course be used for other articles than the absorbent garment shown in FIG. 1. For example can a hooks member provided on a tab for a diaper be provided with such an end region, especially if the tab is made of a nonwoven material.

The invention claimed is:

1. A sanitary, absorbent article comprising:
   a hooks and loops fastener for overlappingly attaching opposite first and second side parts of the article to each other, the article having a first position where a portion of the first side part extends over a portion of the second side part and the first and second side parts are attached to each other so that a free edge of the first side part is distanced from a free edge of the second side part of the article,
   when in the first position, a hooks fastener member is affixed to the first side part in an area thereof overlapping a loops section of the second side part;
   at least the hooks fastener member has a base portion having a bottom surface, the entire bottom surface overlaying and being affixed to the first side part of the article and the base portion having an opposite top surface containing hook elements, the base portion having a first free end edge distal from the free edge of the first side part and a second free end edge at a location proximate to the free edge of the first side part, wherein the base portion exists only between the first free end edge and the second free end edge,
   the base portion includes a first region extending from the first free end edge thereof toward the second free end edge and a second region extending from the second free end edge thereof toward the first region such that the second region is closer to the free edge of the first side part than the first region;
   the hook elements on the hooks fastener member are arranged on the base portion so that the second region is able to engage the loops fastener member with a greater strength than the first region.

2. The article according to claim 1, wherein the first region of the hooks fastener member has a width of 3-8 mm.

3. The article according to claim 1, wherein the hooks fastener member is without hooks elements in the first region.

4. The article according to claim 3, wherein the loops member is without loops elements in a portion thereof complementary to the first region of the hooks member.

5. The article according to claim 1, wherein the hook elements of the hooks fastener member are made non-engageable with loops elements of the loops fastener member or vice versa in the portion of the hooks and loops fastener in which the first region of the hooks fastener member is disposed.

6. The article according to claim 1, wherein the hooks member is affixed to a nonwoven material.

7. The article according to claim 1, wherein the first region of the hooks fastener member has a width of 5 mm.

8. The article according to claim 1, wherein the first side part of the article is a belt part and the second side part of the article is a belt part, the belt parts laterally protruding from a central part of the article and connecting to a waist part of the article and being dimensioned so as to connect to one another around a wearer.

9. The article according to claim 1, wherein the first side part of the article is a belt part and the second side part of the article is a belt part, the belt parts laterally protruding from side parts of the article.

10. A sanitary, absorbent article comprising:
  a hooks and loops fastener for overlappingly attaching opposite first and second parts of the article to each other, the article having a first position where a portion of the first part extends over a portion of the second part and the first and second parts are attached to each other so that a free edge of the first part is distanced from a free edge of the second part of the article,
  when in the first position, a hooks fastener member is affixed to the first part in an area thereof overlapping a loops section of the second part;
  at least the hooks fastener member has a base portion having a bottom surface and the entire bottom surface overlaying and being affixed to the first part of the article and an opposite top surface contains hook elements, the base portion having a first free end edge distal from the free edge of the first part and a second free end edge at a location proximate to the free edge of the first part, wherein the base portion exists only between the first free end edge and the second free end edge,
  the base portion includes a first region extending from the first free end edge thereof toward the second free end edge and a second region extending from the second free end edge thereof toward the first region such that the second region is closer to the free edge of the first part than the first region;
  the hook elements on the hooks fastener member are arranged on the base portion so that the second region is able to engage the loops fastener member with a greater strength than the first region.

11. The article according to claim 10 wherein the first region of the hooks fastener member has a width of 3-8 mm.

12. The article according to claim 10 wherein the hooks fastener member is without hooks elements in the first region.

13. The article according to claim 12, wherein the loops section is without loops elements in a portion thereof complementary to the first region of the hooks member.

14. The article according to claim 10, wherein the hook elements of the hooks fastener member are made non-engageable with loops elements of the loops fastener member or vice versa in the portion of the hooks and loops fastener in which the first region of the hooks fastener member is disposed.

15. The article according to claim 10, wherein the hooks member is affixed to a nonwoven material.

16. The article according to claim 1, wherein the first region of the hooks fastener member has a width of 5 mm.

17. The article according to claim 10, wherein the first part of the article is a belt part and the second part of the article is a belt part, the belt parts laterally protruding from a central part of the article and connecting to a waist part of the article and being dimensioned so as to connect to one another around a wearer.

18. The article according to claim 10, wherein the first part of the article is a belt part and the second part of the article is a belt part, the belt parts laterally protruding from side parts of the article.

* * * * *